US008431524B2

(12) United States Patent
Santos Savio et al.

(10) Patent No.: US 8,431,524 B2
(45) Date of Patent: Apr. 30, 2013

(54) PEPTIDE ANTAGONIST OF INTERLEUKIN-15 ACTIVITY

(75) Inventors: Alicia Santos Savio, Ciudad de la Habana (CU); Osvaldo Reyes Acosta, Ciudad de la Habana (CU); Haydee Geronimo Perez, Ciudad de la Habana (CU); Hilda Elisa Garay Perez, Ciudad de la Habana (CU); Yunier Rodriguez Alvarez, Ciudad de la Habana (CU); Gerardo Enríque Guillen Nieto, Ciudad de la Habana (CU)

(73) Assignee: Centro de Ingenieria Genetica y Biotecnologia, Ciudad de La Habana (CU)

( * ) Notice: Subject to any disclaimer, the term of this patent is extended or adjusted under 35 U.S.C. 154(b) by 0 days.

(21) Appl. No.: 13/120,855

(22) PCT Filed: Sep. 30, 2009

(86) PCT No.: PCT/CU2009/000006
§ 371 (c)(1),
(2), (4) Date: Jun. 21, 2011

(87) PCT Pub. No.: WO2010/037351
PCT Pub. Date: Apr. 8, 2010

(65) Prior Publication Data
US 2011/0251140 A1    Oct. 13, 2011

(30) Foreign Application Priority Data

Sep. 30, 2008    (CU) .................................. 2008-0184

(51) Int. Cl.
*A61K 38/04*     (2006.01)
*C12Q 1/68*      (2006.01)

(52) U.S. Cl.
USPC ............. 514/1.1; 530/328; 530/351; 435/6.1; 435/320.1

(58) Field of Classification Search ........................ None
See application file for complete search history.

(56) References Cited

U.S. PATENT DOCUMENTS

| | | | |
|---|---|---|---|
| 6,001,973 | A | 12/1999 | Strom et al. |
| 6,013,480 | A | 1/2000 | Grabstein et al. |
| 6,168,783 | B1 | 1/2001 | Grabstein et al. |
| 6,177,079 | B1 | 1/2001 | Grabstein et al. |
| 2004/0253587 | A1 | 12/2004 | Grabstein et al. |

FOREIGN PATENT DOCUMENTS

| | | |
|---|---|---|
| EP | 1801119 A1 | 6/2007 |
| WO | 9741232 | 11/1997 |
| WO | 0102003 A1 | 1/2001 |
| WO | 03017935 A2 | 3/2003 |
| WO | 2005085282 A1 | 9/2005 |
| WO | 2006029578 A1 | 3/2006 |

OTHER PUBLICATIONS

Budagian et al., "Reverse Signaling through Membrane-bound Interleukin-15", Journal of Biological Chemistry, vol. 279, No. 40, pp. 42192-42201; 2004.
Cosman et al., "Cloning, Sequence and Expression of Human Interleukin-2 Receptor", Nature, vol. 312, pp. 768-771; 1984.
Ruchatz et al., "Soluble IL-15 Receptor alpha-Chain Administration Prevents Murine Collagen-Induced Arthritis: A Role for IL-15 in Development of Antigen-Induced Immunopathology", Journal of Immunology, vol. 160, pp. 5654-5660; 1998.
Ferrari-Lacraz et al., "Targeting IL-15 Receptor-Bearing Cells with an Antagonist Mutant IL-15/Fc Protein Prevents Disease Development and Progression in Murine Collagen-Induced Arthritis", Journal of Immunology, vol. 173, pp. 5818-5826; 2004.
Ziolkowska et al., "High Levels of IL-17 in Rheumatoid Arthritis Patients: IL-15 Triggers In Vitro IL-17 Production Via Cyclosporin A-Sensitive Mechanism", Journal of Immunology, vol. 164, pp. 2832-2838; 2000.
Ruckert et al., "Inhibition of Keratinocyte Apoptosis by IL-15: A New Parameter in the Pathogenesis of Psoriasis?", Journal of Immunology, vol. 165, pp. 2240-2250; 2000.
Mortier et al., "Natural, Proteolytic Release of a Soluble Form of Human IL-15 Receptor alpha-Chain That Behaves as a Specific, High Affinity IL-15 Antagonist", Journal of Immunology, vol. 173, pp. 1681-1688; 2004.
Bamford et al., "The 5' Untranslated Region, Signal Peptide, and the Coding Sequence of the Carboxyl Terminus of IL-15 Participate in its Multifaceted Translational Control", Journal of Immunology, vol. 160, pp. 4418-4426; 1998.
Pettit et al., "Structure-Function Studies of Interleukin 15 using Site-specific Mutagenesis, Polyethylene Glycol Conjugation, and Homology Modeling", Journal of Biological Chemistry, vol. 272, No. 4, pp. 2312-2319; 1997.
Kim et al., "Targeting the IL-15 Receptor with an Antagonist IL-15 Mutant/Fe γ2a Protein Blocks Delayed-Type Hypersensitivity", Journal of Immunology, vol. 160, pp. 5742-5748; 1998.
Lorenzen et al., "The Structure of the Interleukin-15 alpha Receptor and its Implications for Ligand Binding", Journal of Biological Chemistry, vol. 281, No. 10, pp. 6642-6647; 2006.
Grabstein et al., "Cloning of a T Cell Growth Factor that Interacts with the Beta Chain of the Interleukin-2 Receptor", Science, vol. 264, pp. 965-968; 1994.
Burton et al., "A Lymphokine, Provisionally Designated Interleukin T and Produced by a Human Adult T-cell Leukemia Line, Stimulates T-cell Proliferation and the Induction of Lymphokine-Activated Killer Cells", Proc. Natl. Acad. Sci., pp. 4935-4939; 1994.

(Continued)

*Primary Examiner* — Dong Jiang
(74) *Attorney, Agent, or Firm* — Hoffman & Baron, LLP

(57) ABSTRACT

The present invention is related to the field of molecular immunology, particularly to a peptide derived from the sequence of interleukine-15 (IL-15), wherein said peptide was optimized to inhibit the biological activity of this molecule. In the present invention, it is shown that this peptide inhibits IL-15-induced T cell proliferation, Tumor Necrosis Factor α (TNFα) induction and the expression of IL-8 and IL-6 by the IL-15 receptor α subunit (IL-15Rα), all these effects mediated by the binding of the peptide to the IL-15Rα. The invention is also related to the use of the peptide to treat pathologies where the abnormal expression of IL-15 or IL-15Rα is related to the course of the disease, such as rheumatoid arthritis (RA) and prostate cancer.

9 Claims, 3 Drawing Sheets

OTHER PUBLICATIONS

Kurys et al., "The Long Signal Peptide Isoform and its Alternative Processing Direct the Intracellular Trafficking of Interleukin-15", Journal of Biological Chemistry, vol. 275, No. 39, pp. 30653-30659; 2000.

Musso et al., "Human Monocytes Constitutively Express Membrane-Bound, Biologically Active, and Interferon-γ-Upregulated Interleukin-15", Blood, vol. 93, No. 10, pp. 3531-3539; 1999.

Burkett et al., "Coordinate Expression and Trans Presentation of Interleukin (IL)-15R alpha and IL-15 Supports Natural Killer Cell and Memory CD8 T Cell Homeostatis", Journal of Experimental Medicine, pp. 825-834; 2004.

Budagian et al., "Natural Soluble Interleukin-15R alpha is Generated by Cleavage that Involves the Tumor Necrosis Factor-alpha-converting Enzyme (TACE/ADAM17)", Journal of Biological Chemistry, vol. 279, No. 39, pp. 40368-40375; 2004.

Yamada et al., "Pathological Roles of Interleukin-15 in Adult T-Cell Leukemia", Leukemia and Lymphoma, vol. 35, pp. 37-45; 1999.

McInnes et al., "Interleukin 15: A Proinflammatory Role in Rheumatoid Arthritis Synovitis", Immunology Today, vol. 19, No. 2 pp. 75-79; 1998.

McInnes et al., "Interleukin-15 Mediates T Cell-Dependent Regulation of Tumor Necrosis Factor-alpha Production in Rheumatoid Arthritis", Nature Medicine, vol. 3, No. 2, pp. 189-195; 1997.

Yoshihara et al., IL-15 Exacerbates Collagen-Induced Arthritis with an Enhanced CD4+ T Cell Response to Produce IL-17, European Journal of Immunology, vol. 37, pp. 2744-2752; 2007.

Villadsen et al., "Resolution of Psoriasis Upon Blockade of IL-15 Biological Activity in a Xenograft Mouse Model", Journal of Clinical Investigation, vol. 112, No. 10, pp. 1571-1580; 2003.

Mortier et al., "Soluble Interleukin-15 Receptor alpha (IL-15Ralpha)-Sushi as a Selective and Potent Agonist of IL-15 Action Through IL-15RBeta/γ", Journal of Biological Chemistry, vol. 281, No. 3, pp. 1612-1619; 2006.

Rubinstein et al., "Converting IL-15 to a Superagonist by Binding to Soluble IL-15Ralpha", PNAS, vol. 103, No. 24, pp. 9166-9171; 2006.

Bernard et al., "Identification of an Interleukin-15alpha Receptor-Binding Site on Human Interleukin-15", Journal of Biological Chemistry, vol. 279, No. 23, pp. 24313-24322; 2004.

Pettit et al., "Polyethylene Glycol Conjugation to Lysine Residues of Recombinant IL-15 Generates a Specific IL-15 Antagonist", Proceedings of the International Symposium on Controlled Release Bioactive Materials, vol. 22, pp. 496-497; 1995.

Kirman et al., "Increased Number of Interleukin-15-Expressing Cells in Active Ulcerative Colitis", The American Journal of Gastroenterology, vol. 91, No. 9, pp. 1789-1794; 1996.

A

B

C

A

B

SEQUENCE LISTING

```
<160> NUMBER OF SEQ ID NOS: 14

<210> SEQ ID NO 1
<211> LENGTH: 10
<212> TYPE: PRT
<213> ORGANISM: Artificial sequence
<220> FEATURE:
<223> OTHER INFORMATION: Description of the Artificial Sequence: peptide
      that binds to the alpha subunit of IL-15

<400> SEQUENCE: 1

Lys Val Thr Ala Met Lys Cys Phe Leu Leu
1               5                   10

<210> SEQ ID NO 2
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 2

Lys Val Thr Ala Met Lys Cys Phe Leu Ala
1               5                   10
```

```
<210> SEQ ID NO 3
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 3

Lys Val Thr Ala Met Lys Cys Phe Ala Leu
 1               5                  10

<210> SEQ ID NO 4
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 4

Lys Val Thr Ala Met Lys Cys Ala Leu Leu
 1               5                  10

<210> SEQ ID NO 5
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 5

Lys Val Thr Ala Met Lys Ala Phe Leu Leu
 1               5                  10

<210> SEQ ID NO 6
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 6

Lys Val Thr Ala Met Ala Cys Phe Leu Leu
 1               5                  10

<210> SEQ ID NO 7
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 7

Lys Val Thr Ala Ala Lys Cys Phe Leu Leu
 1               5                  10

<210> SEQ ID NO 8
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 8
```

Lys Val Ala Ala Met Lys Cys Phe Leu Leu
1               5                   10

<210> SEQ ID NO 9
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 9

Lys Ala Thr Ala Met Lys Cys Phe Leu Leu
1               5                   10

<210> SEQ ID NO 10
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 10

Ala Val Thr Ala Met Lys Cys Phe Leu Leu
1               5                   10

<210> SEQ ID NO 11
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 11

Lys Val Thr Ala Met Lys Ser Phe Leu Leu
1               5                   10

<210> SEQ ID NO 12
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1 with increased
      biological activity

<400> SEQUENCE: 12

Lys Val Thr Ala Met Thr Cys Phe Leu Leu
1               5                   10

<210> SEQ ID NO 13
<211> LENGTH: 10
<212> TYPE: PRT
<213> ORGANISM: Artificial sequence
<220> FEATURE:
<223> OTHER INFORMATION: Description of the Artificial Sequence:
      synthetic peptide modified from sequence 1

<400> SEQUENCE: 13

Lys Val Thr Ala Met Glu Cys Phe Leu Leu
1               5                   10

<210> SEQ ID NO 14
<211> LENGTH: 10
<212> TYPE: PRT
<213> ORGANISM: Artificial sequence -continued

```
<220> FEATURE:
<223> OTHER INFORMATION: Description of the Artificial Sequence:
      synthetic peptide modified from sequence 1

<400> SEQUENCE: 14

Lys Val Thr Ala Met Thr Cys Tyr Leu Leu
 1               5                   10
```

PEPTIDE ANTAGONIST OF INTERLEUKIN-15 ACTIVITY

CLAIM OF PRIORITY

This application is the U.S. National Phase of, and Applicants claim priority from, International Application Number PCT/CU2009/000006 filed 30 Sep. 2009 and Cuban Patent Application No. 2008-0184 filed 30 Sep. 2008, which are incorporated herein by reference.

INCORPORATION OF SEQUENCE LISTING

Incorporated herein by reference in its entirety is the Sequence Listing for the above-identified Application. The Sequence Listing is disclosed on a computer-readable ASCII text file titled "SequenceListing976_75PCTUS.txt", created on Mar. 24, 2011. The sequence.txt file is 8.85 KB size.

FIELD OF THE INVENTION

The present invention is related to the field of molecular pharmacology, and particularly describes a peptide derived from interleukin-15 (IL-15) that blocks the binding of this cytokine to the alpha subunit of its receptor (IL-15Rα), the peptide being useful to treat diseases involving the abnormal expression of IL-15 and/or IL-15Rα during progression.

PREVIOUS ART

The cytokine known as IL-15 is a 14-15 kDa protein simultaneously identified by two research groups as a T cell activating factor (Grabstein, K. H. et al., Science 1994, 264, 965-968; Burton, J. D. et al., Proc. Natl. Acad. Sci. USA 1994, 91, 4935-4939). The messenger ribonucleic acid (mRNA) of this cytokine is present in a wide range of cells and tissues, but the protein is rarely found in the supernatant of cultured cells is expressing the transcript, due to a strong post-transcriptional control at translational and intracellular trafficking levels (Bamford R N. et al., J. Immunol 1998, 160: 4418-4426; Kurys G, et al., J Biol Chem 2000, 275: 30653-30659. Besides, it has been described that the active form of IL-15 can appear as membrane protein (Musso et al. Blood 1999, 93: 3531-3539), and more recently that it could function both as ligand and as a receptor. The IL-15 acts as a receptor when expressed as integral membrane protein, through the binding of the soluble IL-15Rα, triggering the secretion of the IL-6 and IL-8 pro-inflammatory cytokines, activation of the so-called MAPK and FAK kinases and promoting migration of prostate carcinoma cells (PC-3) that express IL-15 at the cell membrane (Budalgian et al., J. Biol Chem 2004, 40: 42192-42201).

The biological effects of IL-15 are mediated by the binding of this cytokine to a receptor found in the cell membrane comprising three subunits, named α, β and γ. They can be co-expressed in the same cell, or the α subunit-bound IL-15 could be presented to cells expressing the β and γ subunits further inducing the cell signaling by a process known as signaling in trans (Burkett et al. J Exp. Med 2004, 200: 825-834). The IL-15Rβ subunit is shared by the IL-2, a cytokine showing a high structural homology with IL-15, and the IL-15Rβ subunit is also shared with other cytokines, such as IL-2, IL-4, IL-7, IL-9, IL-21. The IL-15Rα subunit is specific for the IL-15, mediating a very high affinity binding (Kd= $10^{-11}$) and can be found either as membrane receptor or in soluble form (Budagian V. et al. J Biol Chem. 2004 24:40368-75; Mortier et al. J. Immunol 2004, 173: 1681-1688).

High levels of IL-15 expression have been associated to the pathogenesis of autoimmune and inflammatory diseases, like in Crohn's disease (Kirman I., Am. J. Gastroenterol. 1996, 91: 1789-1794), psoriasis (Rückert R. J. Immunol 2000, 165: 2240-2250), leukemias (Yamada Y. Leukemia and Limphoma 1999, 35: 37-45 and rheumatoid arthritis (RA) (McInnes I. B., Immunology Today 1998, 19: 75-79).

In RA, McInnes et al. found abnormal IL-15 expression, high concentrations of IL-15 in the synovial fluid and IL-15 expression in synovial membrane cells. They suggested that IL-15 precedes the tumor necrosis factor α (TNFα) in the cytokines cascade, proposing a cellular contact-mediated mechanism for the induction by IL-15-activated T cells of TNFα synthesis in macrophages. They also proposed that IL-15 acts as a very relevant factor in T cell migration towards the synovial fluid. (McInnes et al., Nat Med 1997, 3: 189-195). Ziolkowska et al. reported that IL-15 induces the expression of IL-17 in the joints of RA patients, and it is also known that this cytokine stimulates the secretion of inflammation mediators such as IL-6 and IL-8, granulocytes macrophages colony-stimulating factor and the E2 prostaglandin by synovial cells, suggesting a significant role for IL-15 in RA pathogenesis (Ziolkowska et al., J Immunology 2000, 164: 2832-2838). Recently, it was demonstrated that IL-15 exacerbates collagen-induced arthritis (CIA) in a mouse transgenic for this cytokine Yoshihara et al., Eur J. Immunol. 2007, 37: 2744-2752). All these elements suggest that an antagonist of IL-15 could be a potential therapeutic to treat RA and other autoimmune and inflammatory diseases.

It has been previously described that the aspartic acid residue at position 56 in the IL-15 molecule is relevant for binding to the IL-15Rβ, and glutamine at position 156 for binding to the IL-15Rγ subunit. Mutated proteins, also called muteins, behave as molecules antagonizing IL-15 that bind the IL15-Rα and hamper signal transduction from IL-15Rβ and γ subunits. Antibodies recognizing these aminoacids (aa.) also act as IL-15 antagonists (U.S. Pat. No. 6,177,079, U.S. Pat. No. 6,168,783, U.S. Pat. No. 6,013,480, U.S. Pat. No. 6,001,973, U.S. Pat. No. 9,706,931, International patent application No. WO9741232).

The use of antagonists for this cytokine has proven useful in animal models of psoriasis (Villadsen L. S. et al. J. Clin. Invest. 2003, 112: 1571-1580) and RA (Ferrari-Lacraz S. et al, J. Immunol 2004, 173: 5818-5826).

Ruchatz et al. generated a soluble fragment of murine IL-15Rα that inhibited CIA when administered to DBA/1 mice (Ruchatz H, J. Immunology 1998, 160: 5654-5660). It was subsequently found that IL-15Rα can act as a potent agonist of IL-15 biological function (Mortier E. J. Biol. Chem. 2006, 281:1612-1619; Rubinstein M P, PNAS USA 2006, 103: 9166-9171).

Genmab owns a patent on antibodies specific for IL-15 (Patent application No. WO03017935) describing four antibodies. Two of them, named 146B7 and 146H5, target the IL-15 region interacting with the IL-15Rγ and inhibit the IL-15-induced cell proliferation in the CTLL-2 cell line and peripheral blood mononuclear cells (PBMC). That patent also describes the 404A8 and 404E4 antibodies that do not inhibit cell proliferation. Of those four antibodies, 146B7 is being tested in a Phase II clinical trial for RA by the Amgen company, denominated AMG714.

Bernard et al. identified in 2004 two sequences of the IL-15 molecule for binding to IL15-Rα. Those sequences comprise aminoacids 44 to 52 and 64 to 68 in the mature protein, and they also described muteins that could act as agonists or antagonists of IL-15 (Bernard J. et al. J Biol Chem 2004, 279: 24313-24322).

Santos et al. described a IL-15 antagonistic peptide (Patent application No. WO2006/029578). The use of a small size (10 aa.) peptide as an antagonist of IL-15 is advantageous due to its selective blocking of the IL-15 binding to the IL-15Rα, also mediating or avoiding the effects of that interaction.

However, the identification of peptide sequences of higher solubility and enhanced biological activity to antagonize IL-15 compared to the previously mentioned peptide is particularly relevant.

DETAILED DESCRIPTION OF THE INVENTION

This invention contributes to solve the abovementioned problem by providing a more soluble and active peptide than that described in the Patent application No. WO2006/029578, decreasing its inhibitory concentration 50 ($IC_{50}$), that is the concentration of the substance generating a 50% of inhibition, from 130 μM to 8 μM by substituting Thr for the second Lys and obtaining a peptide dimer. Said sequence, SEQ ID No. 12, is synthesized as a 10 aa. linear peptide, interacting with the IL-15Rα and showing IL-15 antagonist capacity.).

The said peptide was optimized by point aminoacid substitutions to identify the aminoacids essential for its antagonistic activity for IL-15. Specifically for the second Lys, substitutions affecting the charge such as replacing it with a neutral Thr residue or a negatively charged Glu aminoacid, a ten-fold antagonistic activity was obtained for this peptide. Besides, it was found that the dimer formed between two peptide molecules linked through the free cystein was seven times more active than the monomer.

A peptide ten times more active in the IL-15-dependent proliferation assay of the CTLL-2 cell line was obtained, resulting from the substitution previously mentioned. This peptide also retains the capacity to bind to the IL-15Rα.

The resulting peptide, which is the aim of the present invention, comprises the peptide sequence described as SEQ ID No. 12 in the list of sequences. The increased activity found after the indicated Lys to Thr aminoacid change was surprising. Such an increase in the biological activity of the peptide after the change on its primary sequence was unexpected for any people skilled in the art on this field of technique, based on previous findings, as demonstrated in the examples of the embodiments of the present invention.

The chemically synthesized peptide dimer obtained by the linkage of monomers identified in the List of sequences as SEQ ID No. 12 through the free Cys was seven times more active than the monomer and 15 times more active than the original peptide described in patent No. WO2006/029578.

The peptide identified with the aminoacid sequence listed as SEQ ID No. 12 can inhibit the reverse signaling effect through the membrane IL-15 reported by Budalgian et al. in 2004 (Budalgian et al., J. Biol Chem 2004, 40: 42192-42201), through binding of said peptide to the soluble alpha chain.

The present invention comprises the use of said peptide to treat RA, alone or combined with any other appropriate molecule, such as steroid anti-inflammatory drugs (e.g., corticosteroids) and drugs modifying the course of disease (e.g., methotrexate).

Another embodiment of the present invention comprises the topical use of this peptide to treat skin diseases in which lesions IL-15 is detected during the course of disease, such as psoriasis and cutaneous T cell lymphoma.

In another embodiment of the present invention, the peptide is used to inhibit the binding of the soluble IL-15Rα to the IL-15 expressed in the tumor cell membrane and to inhibit tumor cell migration.

The peptide subject of the present invention can be a linear peptide or form a dimer, mainly characterized by its activity antagonistic of IL-15. On the other hand, the in vitro effect of the peptide subject of the present invention is demonstrated in a cell proliferation assay of the CTLL-2 murine cell line and the human lymphocytic Kit225 leukemia cell line.

The peptide describe in the present invention was identified by Ala scanning of the peptide described in the patent application No. WO2006/029578. Each mutated peptide was chemically synthesized by the solid phase synthesis method. The resulting peptides were purified by high performance liquid chromatography (HPLC) and analyzed by mass spectrometry, for more than 95% of purity. Each peptide was evaluated for the effectiveness to inhibit the biological activity of IL-15.

The peptide subject of the present invention inhibits the expression of IL-8 induced by the IL-15Rα. This same peptide inhibits the expression of IL-6 and the release of tumor necrosis factor alpha (TNFα) induced by the IL-15Rα.

In another embodiment of the present invention the peptide is obtained by genetic manipulation or by chemical synthesis. In an embodiment of the present invention the peptide is obtained as a dimer formed between two molecules of the peptide comprising the aminoacid sequence identified as SEQ ID No. 12. In a particular embodiment, the dimer is obtained from two peptide molecules dimerized through the free cystein.

Is also subject of the present invention the deoxyribonucleic acid (DNA) coding for the peptide with the sequence listed as SEQ ID No. 12, its expression product being able to bind the IL-15Rα or its soluble fraction, inhibiting the biological activity of IL-15. In an embodiment of the present invention, a vector bearing said DNA sequence can be used for the expression of the peptide sequence. The results obtained suggest the use of the peptide claimed in the present invention as therapeutic tool to treat diseases as those previously mentioned, which are characterized by an over-expression of IL-15 and justify the use of IL-15 antagonists.

Therefore, is also subject of the present invention a therapeutic pharmaceutical composition able of inhibiting the biological activity of IL-15 that depends on the IL-15Rα, wherein said pharmaceutical composition comprises the aminoacid sequence described in the List of sequences as SEQ ID No. 12. In an embodiment of the resent invention, the therapeutic pharmaceutical composition comprises the peptide dimerized. In another embodiment of the invention, the therapeutic pharmaceutical composition able of inhibiting the IL-15Rα-dependent biological activity of IL-15 comprises the peptide as a monomer or as a dimer, conjugated or mixed with acceptable pharmaceutical excipients. In another embodiment, the therapeutic pharmaceutical composition able of inhibiting the IL-15Rα-dependent biological activity of IL-15 contains the nucleic acid strand coding for the said peptide (SEQ ID No. 12).

Is also a subject of the present invention the use of a peptide comprising the aminoacid sequence described in the List of sequences as SEQ ID No. 12 to manufacture a medicine to treat rheumatoid arthritis, Crohn's disease, psoriasis and prostate cancer.

BRIEF DESCRIPTION OF DRAWINGS

FIG. 1A: Evaluation of peptides SEQ ID No. 4 and SEQ ID No. 5; FIG. 1B: Evaluation of peptides SEQ ID No. 2 and SEQ ID No. 3; FIG. 1C: Evaluation of peptides SEQ ID No. 7, SEQ ID No. 8 and SEQ ID No. 9.

DETAILED DESCRIPTION OF REALIZATION/EXAMPLES FOR REALIZATION

Figure 1:
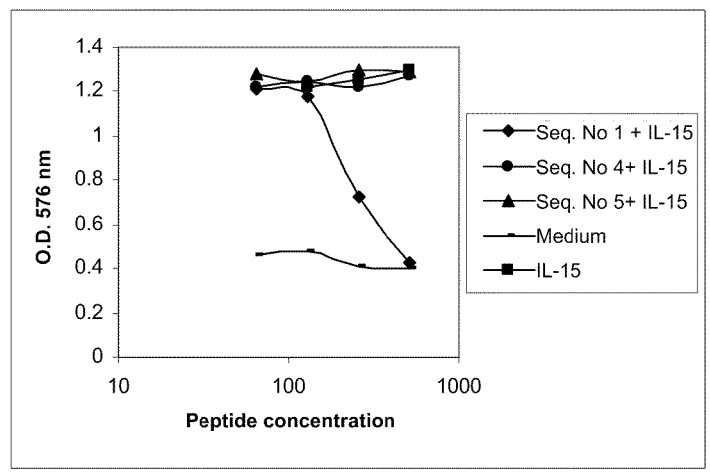
FIG. 1. Effect of different concentrations of the peptide on the IL-15-induced proliferation of the CTLL-2 cell line. CTLL-2 cells were incubated with 300 pg/mL of IL-15 combined with serial dilutions of the peptides. Proliferation was measured by using mitochondrial staining with 3-(4,5-dimethylthiazol-2-yl)-2,5-diphenyl tetrazolium bromide (MTT).
Figure 1:
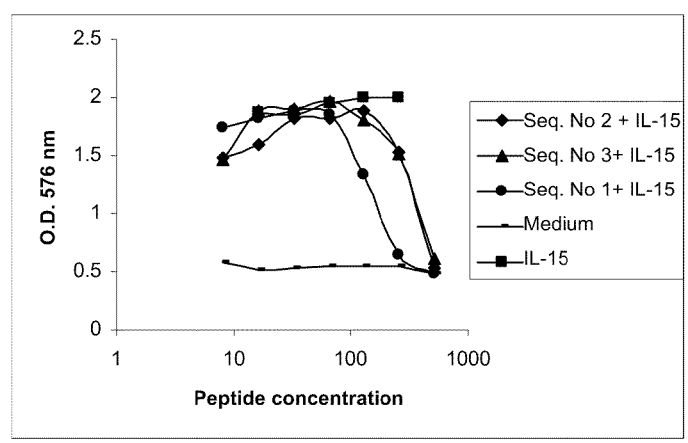
Figure 1:
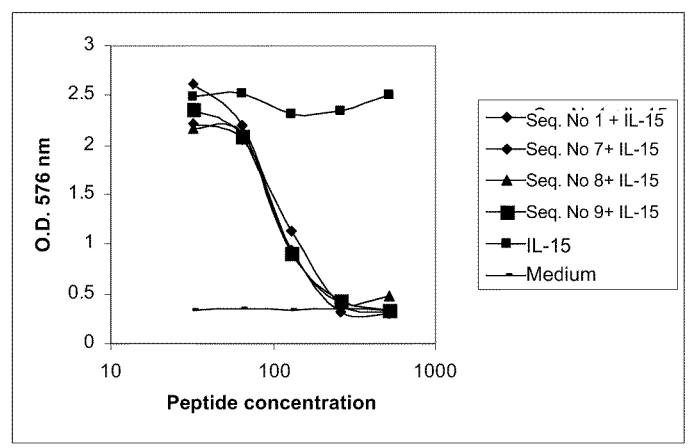

The present invention is explained through the following realización examples:

Example 1

Optimizing of an IL-15 Peptide that Binds to the IL-15Rα and Inhibits the Biological Function of IL-15

Design

A panel of peptides was design by substituting each aminoacid on the sequence of the peptide claimed in the patent application No. WO2006/029578 by the alanine (Ala) aminoacid. In another set of peptides, cysteine (Cys) was substituted by Ser and Lys by Thr or Glu.

Peptide Synthesis

The peptides were synthesized by using the Fmoc/tBu strategy in syringes. The Fmoc-AM-MBHA resin was used at 0.54 mmol/g and the synthesis procedure was carried out under mechanical agitation. The peptides were treated with trifluoroacetic acid and lyophilized, and further characterized by HPLC and mass spectrometry. All the peptides were obtained with more than 95% of purity and their corresponding masses were as expected for their aminoacid sequence.

Example 2

Effect of the Peptides Described on the Proliferation of the CTLL-2 and KiT225 Cell Lines The CTLL-2 and KiT225 cell lines depend on IL-15 and proliferate when this cytokine is present. Those molecules able to bind IL-15 and that blocking signal transduction from the IL-15R inhibit proliferation of these two cell lines.

To evaluate the neutralizing capacity of the peptides of the present invention, serial dilutions of these peptides were carried out in 96-well plates (Costar, USA) in a 25 μL volume of RPMI medium (Gibco) supplemented at 10% with calf fetal serum (Gibco). Previously washed CTLL-2 or KiT225 cells were added at $5\times10^3$ cells/well and incubated for 30 min, and a saturating amount of 300 pg/mL IL-15 was added per well.

The antagonistic activity of the peptides was also evaluated, by varying the concentration of IL-15 at a fix concentration of 260 μM of each peptide. Incubation was carried out for 72 h at 37° C. and 5% $CO_2$. Proliferation was assessed by using the MTT mitochondrial staining method (Cosman et al., Nature 1984, 312: 768-771). MTT is reduced to red formazan by the mitochondrial dehydrogenase of live cells. The $IC_{50}$ was determined to each peptide at a IL-15 concentration of 300 pg/mL.

TABLE 1

List of peptides evaluated and values of $IC_{50}$ obtained in the proliferation assay for the CTLL-2 cell line.

| Peptide | $IC_{50}$ (μM) |
| --- | --- |
| KVTAMKCFLL | 130 |
| KVTAMKCFLA | 260 |
| KVTAMKCFAL | 200 |
| KVTAMKCALL | 0 |
| KVTAMKAFLL | 0 |
| KVTAMACFLL | n.d |
| KVTAAKCFLL | 130 |
| KVAAMKCFLL | 130 |
| KATAMKCFLL | 130 |
| AVTAMKCFLL | n.d |
| KVTAMKSFLL | 0 |
| KVTAMTCFLL | 24.6 |
| KVTAMECFLL | 0 |
| KVTAMTCYLL | 57.7 | n.d: Not determined

This assay was used to evaluate all the peptides, allowing to obtain the $IC_{50}$ values shown in table 1. The $IC_{50}$ values show the loss of the inhibitory effect of the peptide in the Cys-Ala, Cys-Ser, Phe-Ala and Gly-Glu mutants; and this effect is affected in almost 50% in the Leu-Ala mutants. A five-fold inhibitory activity is obtained for the Lys-Thr mutant and 15-fold in the dimeric form of the Lys-Thr mutant.

Figure 3:
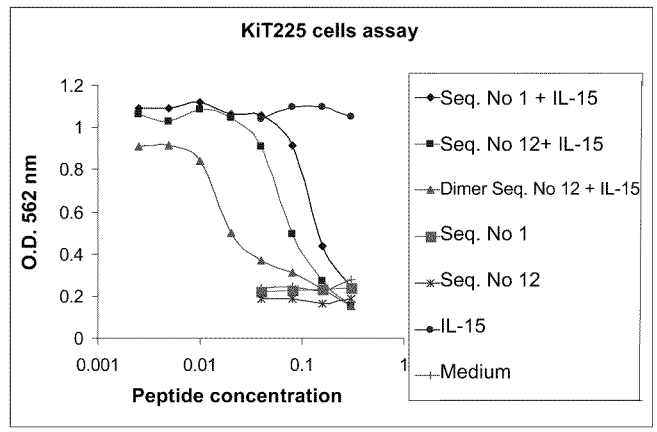
FIG. 3. Effect of different peptide concentrations on the IL-15-induced proliferation of the KiT225 cell line. The Kit225 cells were incubated with IL-15 at 300 pg/mL, combined with serial dilutions of peptides. Proliferation was measured by using the MTT mitochondrial staining.

FIGS. 1A, 1B and 1C represent the behavior of the optical density (O.D.) at 576 nm for the different peptide concentrations of the Phe-Ala, Cys-Ala, Leu1-Ala, Leu2-Ala, Met-Ala, Thr-Ala and Val-Ala mutants. FIG. 3 shows the behavior of the Lys-Thr mutant as monomer and dimer, showing an inhibitory effect depending on the concentration of the peptide and a higher inhibitory effect for the dimer of the Lys-Thr mutant.

Figure 4:
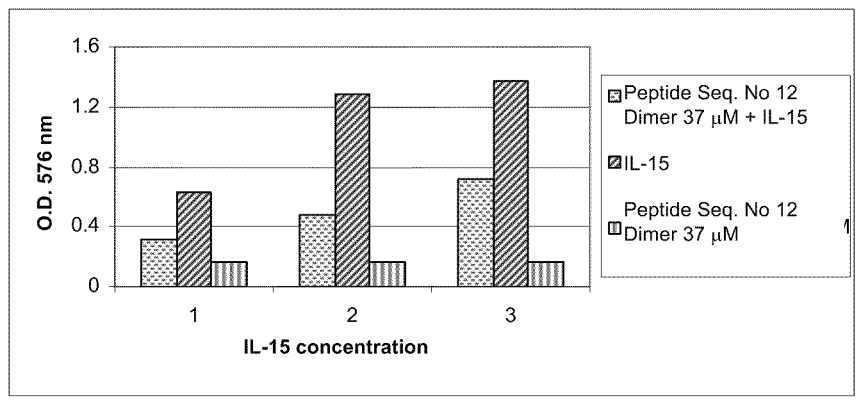
FIG. 4. Effect of the peptide on the proliferation of the CTLL-2 cell line induced by different concentrations of IL-15 at a fixed peptide concentration. The IL-15 concentrations were 75 pg/mL (1); 150 pg/mL (2); 300 pg/mL (3).

The antagonistic activity of the peptides was also evaluated by varying IL-15 concentration at a fixed peptide concentration. FIG. 4 shows the dependence of the antagonistic activity of the mutant Lys-Thr peptide on the IL-15 concentration.

Example 3

Figure 2:
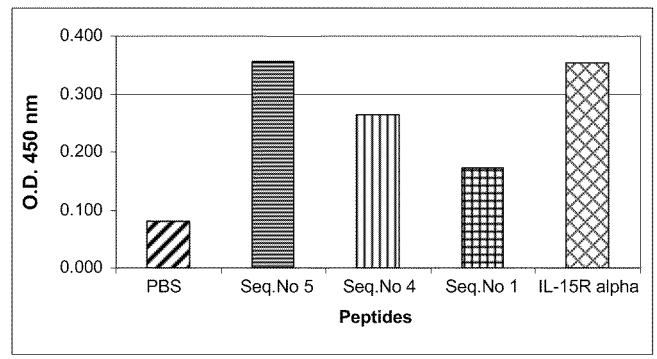
FIG. 2. Diagram representing peptide binding of human IL-15Rα. The displacement of binding of IL-15 to IL-15Rα by the peptides was evaluated by ELISA.

Competition ELISA to Study the Capacity of the Peptides to Displace the Binding to IL-15Ra Peptide binding to the IL15-Rα was characterized by ELISA. Briefly, 96-well plates were coated with purified IL-15 in phosphate buffered saline (PBS) and blocked with bovine albumin at 1% in PBS. Dilutions of each peptide were added to the wells and plates were incubated for 1 h at 37° C. The plates were washed with PBS-Tween 20 and incubated with an IL-15Rα-Fc for 1 h at 37° C. Plates were washed again with PBS-Tween 20 and further incubated an anti Fc-human IgG-peroxidase conjugate for 1 h at 37° C. After washing, the antigen-antibody reaction was run by adding the substrate and 3,3',5,5'-Tetramethylbenzidine (TMB), and O.D. was read at 450 nm. Results are show in FIG. 2, showing that the Cys-Ala mutant (SEQ ID No. 5) does not displace the binding of IL-15 to the IL15-Rα and the mutant Phe-Ala (SEQ ID No. 4) displaces IL-15 only 10%.

Example 4

Evaluation of the Effect of Peptide (SEQ ID No. 12) on the Expression of IL-6 and IL-8 in the Prostate Cancer Cell Line PC-3

The effect of peptide (SEQ ID No. 12) on the expression of IL-6 and Il-8 was evaluated, such an expression mediated by the binding of Il-15 to the IL15-Rα on the cellular membrane of PC-3 cells (Budagian V., et al. J. Biol. Chem 2004 279: 42192-42201).

The experiment was carried out in 24-well plates by incubating $1.5 \times 10^6$ cells with peptides SEQ ID No. 1 and SEQ ID No. 12 at 100 μg/mL and IL15-Rα (1 ng/mL), and also combinations of IL15-Rα and peptides SEQ ID No. 1 and SEQ ID No. 12.

The RNA was isolated by the TriReagent method (Sigma) and analyzed by measuring the O.D. 260/280 nm ratio and Agarose gel electrophoresis. The real time reverse transcription and polymerase chain reaction were carried out by using the Quantitect Reverse Transcription Kit and QuantiTect SYBR Green PCR (QIAGEN) in a Rotor Gene 6000 equipment.

Figure 5:
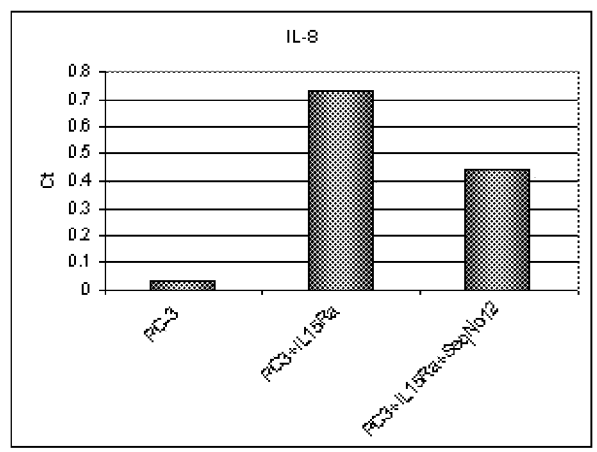
FIG. 5. Diagram showing the inhibitory effect of the peptide on the induction of mRNA of IL-8 (FIG. 5A) and IL-6 (FIG. 5B) in cells of the PC-3 cell line incubated with the IL-15Rα.
Figure 5:
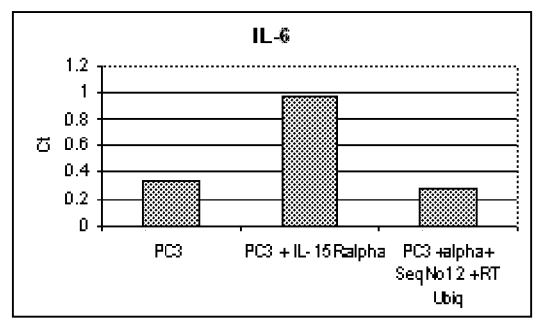

FIGS. 5A and 5B show that the peptide SEQ ID No. 12 inhibits transcription mediated by IL15-Rα of the pro-inflammatory cytokines IL-6 and IL-8.

Example 5

Inhibition of the IL-15-Mediated TNFα Production Induced by the Peptide SEQ ID No. 12 as a Dimer, in Sinovial Fluid Cells of RA Patients After obtaining a written informed consent, synovial fluid from RA patients was extracted and incubated with hyaluronidase at 10 μg per mL of fluid for 45 min at 37° C. Synovial fluid cells were obtained after centrifugation at 1200 rpm for 10 min.

Cells were incubated in 96-well plated at $2 \times 10^5$ cells per well with 50 μg/mL of peptide and 60 ng/mL of IL-15 and also a combination of peptide plus IL-15. After incubation for 48 h, supernatants were collected and stored at −70° C. until evaluation. The amount of TNFα was quantified by EL ISA (R&D DTA50).

Figure 6:
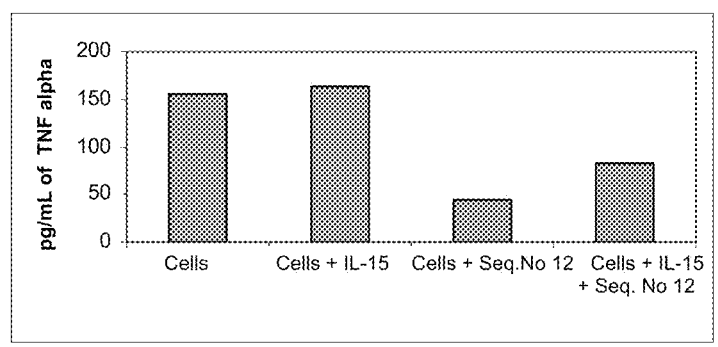
FIG. 6. Inhibition of the release of TNFα by incubating synovial fluid cells with the peptide. Synovial fluid cells from RA patients were simultaneously incubated with IL-15 (100 ng/mL) and the peptide (65 μM) for 48 h. Amounts of TNFα were measured by ELISA. Data of controls showing synovitis caused by trauma are shown.

FIG. 6 shows that peptide SEQ ID No. 12 inhibits TNFα secretion in synovial fluid cells of RA patients Example 6

Xenotransplant SCID Mice Model of Human Psoriasis

Two to three months-old SCID mice were transplanted with a skin graft of 1.5 cm×1.5 cm from a psoriasis patient. Three weeks after, mice were randomized and distributed in three groups: placebo, mice treated with peptide SEQ ID No. 12 at 10 mg/kg of body weight and cyclosporin A at 10 mg/kg in alternate days for two weeks. One week after the last injection, mice were sacrificed and a 4 mm biopsy was taken from each xenotransplant. Biopsies were fixed in formalin for paraffin embedding, and were stained with hematoxilin and eosin dyes (H & E).

As a result, it was observed that the skin grafts from psoriasis patients coming from mice treated with peptide SEQ ID No. 12 or as a dimer show a reduction in the severity of the disease, a significant reduction in the thickness of the epidermis, a significantly decreased number of inflammatory cells and keratinocytes' cycles and a lowered grade of parakeratosis in the psoriatic lesion.

The invention claimed is:

1. An isolated peptide antagonizing the activity of IL-15, said peptide consisting of the amino acid sequence of SEQ ID NO: 12.

2. The peptide according to claim 1, wherein said peptide is obtained by gene manipulation or by chemical synthesis.

3. An isolated peptide homodimer, wherein each molecule consists of the amino acid sequence of SEQ ID NO:12.

4. The peptide homodimer according to claim 3, wherein said dimer is is obtained by dimerization through the free cysteine in the two molecules of the dimer.

5. A pharmaceutical composition comprising a peptide consisting of the amino acid sequence of SEQ ID NO: 12.

6. A pharmaceutical composition comprising a homodimer of a peptide consisting of the amino acid sequence of SEQ ID NO:12.

7. A pharmaceutical composition comprising a monomer or a homodimer of a peptide consisting of the amino acid sequence of SEQ ID NO:12, and pharmaceutically acceptable excipients.

8. As isolated nucleic acid molecule encoding a peptide consisting of the amino acid sequence of SEQ ID NO: 12, wherein the peptide binds to bind to the alpha subunit of the cellular receptor of IL-15 or to its soluble fraction, and inhibits the biological activity of IL-15.

9. A vector comprising the nucleic acid molecule of claim 8.

* * * * *

UNITED STATES PATENT AND TRADEMARK OFFICE
CERTIFICATE OF CORRECTION

PATENT NO. : 8,431,524 B2
APPLICATION NO. : 13/120855
DATED : April 30, 2013
INVENTOR(S) : Santos Savio et al.

It is certified that error appears in the above-identified patent and that said Letters Patent is hereby corrected as shown below:

IN THE SPECIFICATION:

Column 4, line 44

Now reads: "an embodiment of the resent invention";

Should read: -- an embodiment of the present invention --.

Column 7, line 11

Now reads: "IL-6 and II-8 was evaluated";

Should read: -- IL-6 and IL-8 was evaluated --.

Column 7, line 12

Now reads: "the binding of II-15 to the";

Should read: -- the binding of IL-15 to the --.

Signed and Sealed this
Twenty-ninth Day of October, 2013

Teresa Stanek Rea
*Deputy Director of the United States Patent and Trademark Office*